United States Patent
Sato

(10) Patent No.: US 10,321,966 B2
(45) Date of Patent: Jun. 18, 2019

(54) SENSOR STORAGE CONTAINER

(71) Applicant: PHC Holdings Corporation, Tokyo (JP)

(72) Inventor: Yumi Sato, Toon (JP)

(73) Assignee: PHC HOLDINGS CORPORATION, Tokyo (JP)

( * ) Notice: Subject to any disclaimer, the term of this patent is extended or adjusted under 35 U.S.C. 154(b) by 0 days.

(21) Appl. No.: 15/937,421

(22) Filed: Mar. 27, 2018

(65) Prior Publication Data

US 2018/0214231 A1 Aug. 2, 2018

Related U.S. Application Data

(62) Division of application No. 14/394,528, filed as application No. PCT/JP2013/002549 on Apr. 15, 2013, now abandoned.

(30) Foreign Application Priority Data

Apr. 19, 2012 (JP) .................. 2012-095334

(51) Int. Cl.
*B65D 85/38* (2006.01)
*A61B 50/20* (2016.01)
(Continued)

(52) U.S. Cl.
CPC .............. *A61B 50/20* (2016.02); *A61B 50/30* (2016.02); *B65D 43/162* (2013.01); *B65D 51/24* (2013.01);
(Continued)

(58) Field of Classification Search
CPC ....... A61B 50/20; A61B 19/026; A61B 50/30; A61B 25/10; A61B 25/103; A61B 81/266; A61B 83/08; A61B 2543/00083; A61B 2543/00351; A61B 51/24; A61B 83/0005; A61B 2562/0043; A61B 2562/046; B65D 43/162; B65D 83/005; G01N 33/4875
(Continued)

(56) References Cited

U.S. PATENT DOCUMENTS 2,039,559 A 5/1936 Segal
3,091,327 A 5/1963 Lalley
(Continued)

FOREIGN PATENT DOCUMENTS

JP 03-126884 12/1991
JP 2003-146381 5/2003
(Continued)

OTHER PUBLICATIONS

International Search Report, issued in the corresponding PCT Application No. PCT/JP2013/002549, dated Jun. 4, 2013, 2 pages.

*Primary Examiner* — Rafael A Ortiz
(74) *Attorney, Agent, or Firm* — Hamre, Schumann, Mueller & Larson, P.C.

(57) ABSTRACT

This sensor storage container comprises a bottomed cylindrical container body (1) having an opening in its top face, an opening/closing lid (2) provided to the opening of the container body (1) in an openable/closable manner, and an inner case (7) that is open at its top face and provided within the container body (1). The opening/closing lid (2) is linked to the container body (1) via a hinge portion (3), at the peripheral edge of the opening of the container body (1). The inner case (7) is linked on the hinge portion (3) side to the opening/closing lid (2).

4 Claims, 12 Drawing Sheets

(51) Int. Cl.
  *B65D 51/24* (2006.01)
  *G01N 33/487* (2006.01)
  *B65D 83/00* (2006.01)
  *B65D 43/16* (2006.01)
  *A61B 50/30* (2016.01)
  *A61B 5/15* (2006.01)
  *A61B 50/00* (2016.01)

(52) U.S. Cl.
  CPC ....... *B65D 83/005* (2013.01); *B65D 83/0005* (2013.01); *G01N 33/4875* (2013.01); *A61B 5/150022* (2013.01); *A61B 5/150305* (2013.01); *A61B 5/150358* (2013.01); *A61B 2050/0056* (2016.02); *A61B 2562/0295* (2013.01)

(58) Field of Classification Search
  USPC .................................. 206/305, 817, 804, 438
  See application file for complete search history.

(56) References Cited

U.S. PATENT DOCUMENTS

| | | |
|---|---|---|
| 7,387,204 B2 | 6/2008 | Lee |
| 7,955,492 B2 | 6/2011 | Fujiwara et al. |
| 8,236,254 B2 | 8/2012 | Myles et al. |
| 8,524,055 B2 | 9/2013 | Fujiwara et al. |
| 2003/0185708 A1 | 10/2003 | Otake |
| 2007/0138026 A1 | 6/2007 | Fujiwara et al. |
| 2009/0084687 A1 | 4/2009 | Chatelier et al. |
| 2011/0198223 A1 | 8/2011 | Fujiwara et al. |
| 2012/0080330 A1 | 4/2012 | Rush et al. |
| 2014/0158552 A1 | 6/2014 | Fujiwara et al. |

FOREIGN PATENT DOCUMENTS

| | | |
|---|---|---|
| JP | 2011-117912 | 6/2011 |
| JP | 2011-137839 | 7/2011 |
| WO | 2008/122402 | 10/2008 |

SENSOR STORAGE CONTAINER

TECHNICAL FIELD

The present invention relates to a sensor storage container for holding flat sensors.

BACKGROUND ART

The sensors used in measuring blood glucose values, for example, are sometimes carried around by a user, in a state in which a plurality of them are housed in the sensor storage container. The user then takes them out one at time from the sensor storage container for use.

When the sensors are taken out of the sensor storage container, the user grasps the sensor storage container in his hand and tilts or shakes it so that the sensors come out one by one (see Patent Literature 1, for example).

CITATION LIST

Patent Literature

Patent Literature 1: Japanese Laid-Open Patent Application 2003-146381

SUMMARY

With the conventional sensor storage container disclosed in the above publication, there is the risk that the sensors cannot be taken out smoothly with a method in which the sensor storage container is tilted or shaken.

Specifically, with this conventional configuration, a sensor removal opening is provided so that the sensors can be taken out one by one. When the sensor storage container is tilted, etc., however, if a plurality of sensors advance toward the sensor removal opening, the sensors end becoming jammed at the sensor removal opening. As a result, there is a risk that the sensors cannot be taken out smoothly.

In view of this, it is an object of the present invention to provide a sensor storage container with which sensors can be smoothly taken out one by one.

To achieve the stated object, the sensor storage container of the present invention comprises a bottomed cylindrical container body, an opening/closing lid, a hinge portion, an inner case, and a linking body. The container body has an opening in its top face. The opening/closing lid is provided to the opening of the container body in an openable and closable state. The hinge portion links the container body and the opening/closing lid around the peripheral edge of the opening of the container body, and opens and closes the opening/closing lid with respect to the container body. The inner case is provided inside the container body, has an opening in its top face, and holds a plurality of sensors. The linking body links the opening/closing lid with a portion on the hinge portion side of the opening in the inner case.

With the present invention, when the opening/closing lid is opened, the inner case linked to it moves to the opening side within the container body, so the sensors held in the inner case can be exposed from the opening in the container body. As a result, the user can easily grasp one of the sensors exposed from the opening in the container body with his fingers and take that sensor out.

DESCRIPTION OF EMBODIMENTS

The sensor storage container pertaining to an embodiment of the present invention will now be described through reference to the appended drawings.

Embodiment 1

Figure 1:
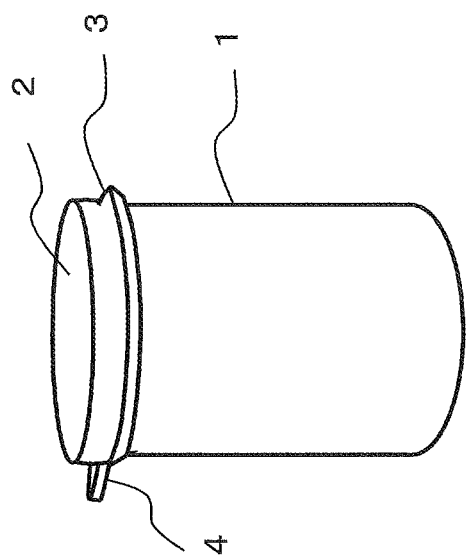
FIG. 1 is an oblique view of the sensor storage container pertaining to Embodiment 1 of the present invention.

The sensor storage container in this embodiment is a container for storing a plurality of biological sample measurement sensors (sensors 8) used to measure a blood glucose value or the like, and as shown in FIG. 1, it comprises a bottomed cylindrical container body 1, an opening/closing lid 2, a hinge portion 3, an inner case 7, and a linking body (linking portion) 9.

The bottomed cylindrical container body 1 has an opening in its top face.

The opening/closing lid 2 is provided to the opening of the container body in an openable and closable state.

The hinge portion 3 links part of the opening/closing lid with the portion of the container body 1 that is around the peripheral edge of the opening.

Figure 2:
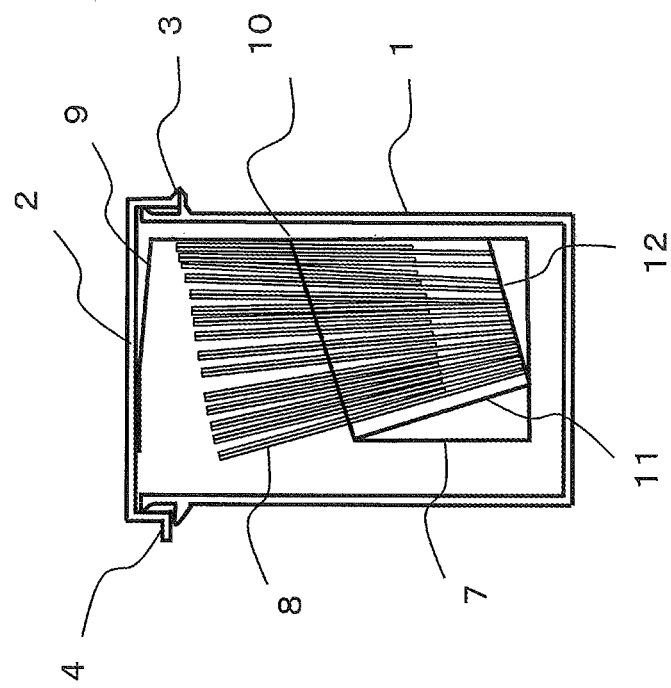
FIG. 2 is a cross section of the sensor storage container in FIG. 1.

That is, the opening/closing lid 2 is linked to the container body 1 via the hinge portion 3 at the peripheral edge of the opening of the container body 1 as shown in FIG. 2. When a lip 4 provided on the opposite side from the hinge portion 3 is lifted up, the opening/closing lid 2 rotates around the hinge portion 3 and goes into its open sate, so that the opening of the container body 1 is exposed to the outside.

Figure 3:
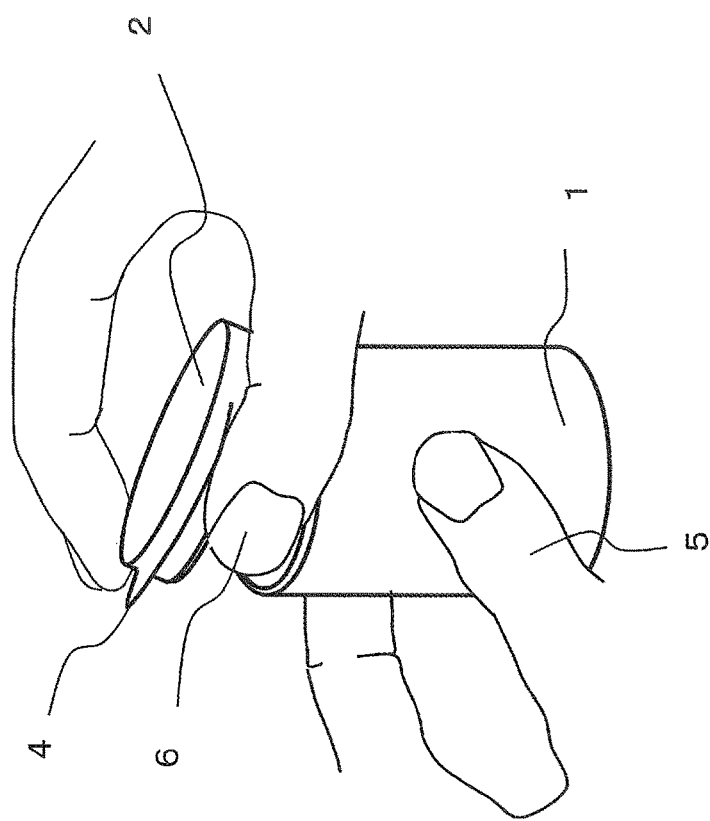
FIG. 3 is an oblique view of the state when the sensor storage container in FIG. 1 has been opened with the fingers.
Figure 4:
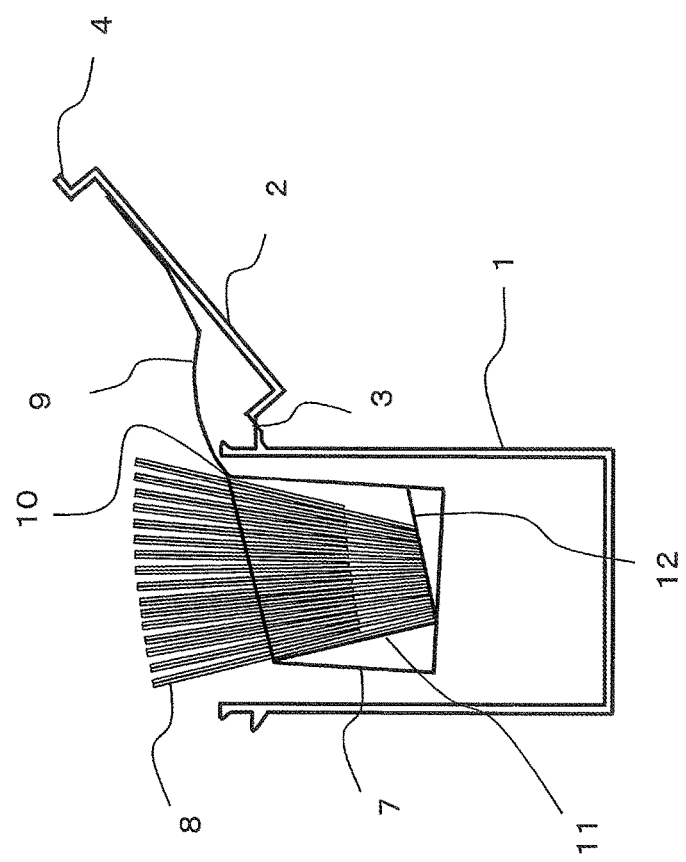
FIG. 4 is a cross section of the sensor storage container in FIG. 1.

FIG. 3 shows the state when the opening/closing lid 2 has been opened part way with respect to the container body 1. At this point, the fingers 5 of the left hand hold the container body 1, while the fingers 6 of the right hand hold the opening/closing lid 2. From this state, when the opening/closing lid 2 is opened further by the fingers 6, the opening/closing lid 2 enters its completely open state with respect to the container body 1, as shown in FIG. 4.

As shown in FIG. 2, the inner case 7 is a bottomed cylindrical case having an opening in its top face, and is housed in the container body 1 in a state of being able to move up and down inside the container body 1 along with the opening and closing of the opening/closing lid 2. As shown in FIGS. 2 and 4, a plurality of the sensors 8 are stored inside the inner case 7.

The linking body 9 is flexible, and links the portion on the hinge portion 3 side of the opening of the inner case 7 with the portion of the opening/closing lid 2 that is away from the end on the hinge portion 3 side. More precisely, a first end of the linking body 9 is linked to the portion on the hinge portion 3 side of the opening of the inner case 7. A second end that is on the opposite side from the first end is linked to the portion of the opening/closing lid 2 that is a specific distance away from the end on the hinge portion 3 side.

That is, the inner case 7 is linked to the opening/closing lid 2 via the flexible linking body 9 on the hinge portion 3 side. Accordingly, as shown in FIG. 2, in a state in which the opening in the top face of the container body 1 has been covered with the opening/closing lid 2, the inner case 7 is supported in the lower space inside the container body 1. In this state, the upper ends of the sensors 8 are housed within the container body 1.

In contrast, as shown in FIG. 4, in a state in which the opening/closing lid 2 is fully open with respect to the top face opening of the container body 1, the second end of the linking body 9 moves out of the top face of the container body 1 along with the opening/closing lid 2, as the opening/closing lid 2 opens. As a result, the inner case 7 is pulled up by the linking body 9 and moves upward within the container body 1. In this state, the upper ends of the sensors 8 protrude above the top face opening of the container body 1.

Consequently, when a sensor 8 is taken out of the sensor storage container, the upper ends of the sensors 8 pop up from the opening and are released, making them easier to remove.

Also, as shown in FIG. 2, with the sensor storage container in this embodiment a sloped side face 11 whose lower part is on a linking portion 10 side and whose upper part is on the opposite side from the linking portion 10 is provided to the inner face of the inner case 7 on the opposite side from the linking portion 10 going to the opening/closing lid 2.

Consequently, as shown in FIGS. 2 and 4, of the sensors 8 inserted into the inner case 7, the sensor 8 held on the opposite side from the linking portion 10 is supported in a state of being inclined toward the lip 4 side with respect to the vertical direction.

Furthermore, with the sensor storage container in this embodiment, a sloped bottom face 12, which is higher on the linking portion 10 side and is lower on the opposite side from the linking portion 10 side, is provided to the bottom face of the inner case 7.

In other words, the sloped bottom face 12 is provided so as to slope downward from the linking portion 10 side toward the opposite side, in the bottom portion of the inner case 7.

As shown in FIGS. 2 and 4, the sensors 8 inserted into the inner case 7 are held in a state in which they are leaning over to the lip 4 side with respect to the vertical direction.

In this embodiment, the above-mentioned sloped side face 11 and sloped bottom face 12 are used to adjust the state in which the sensors 8 are held, so in a state in which the opening/closing lid 2 is open and the inner case 7 has risen up through the container body 1, the upper ends of the sensors 8 are spread apart more than the lower ends, as shown in FIG. 4.

Figure 5:
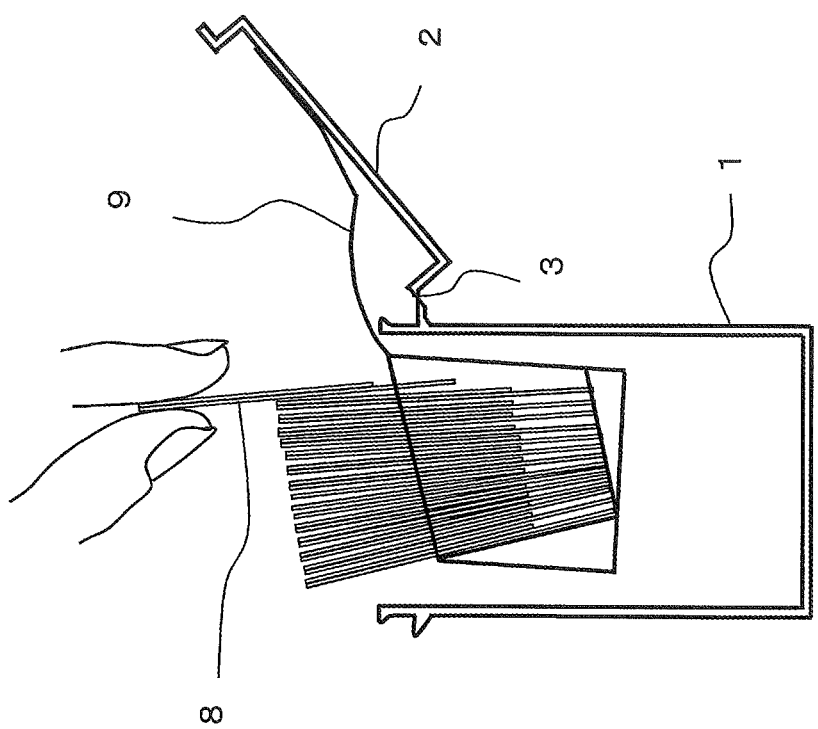
FIG. 5 is a cross section of the state when a sensor is taken out with the fingers from the sensor storage container in FIG. 1.
Figure 6:
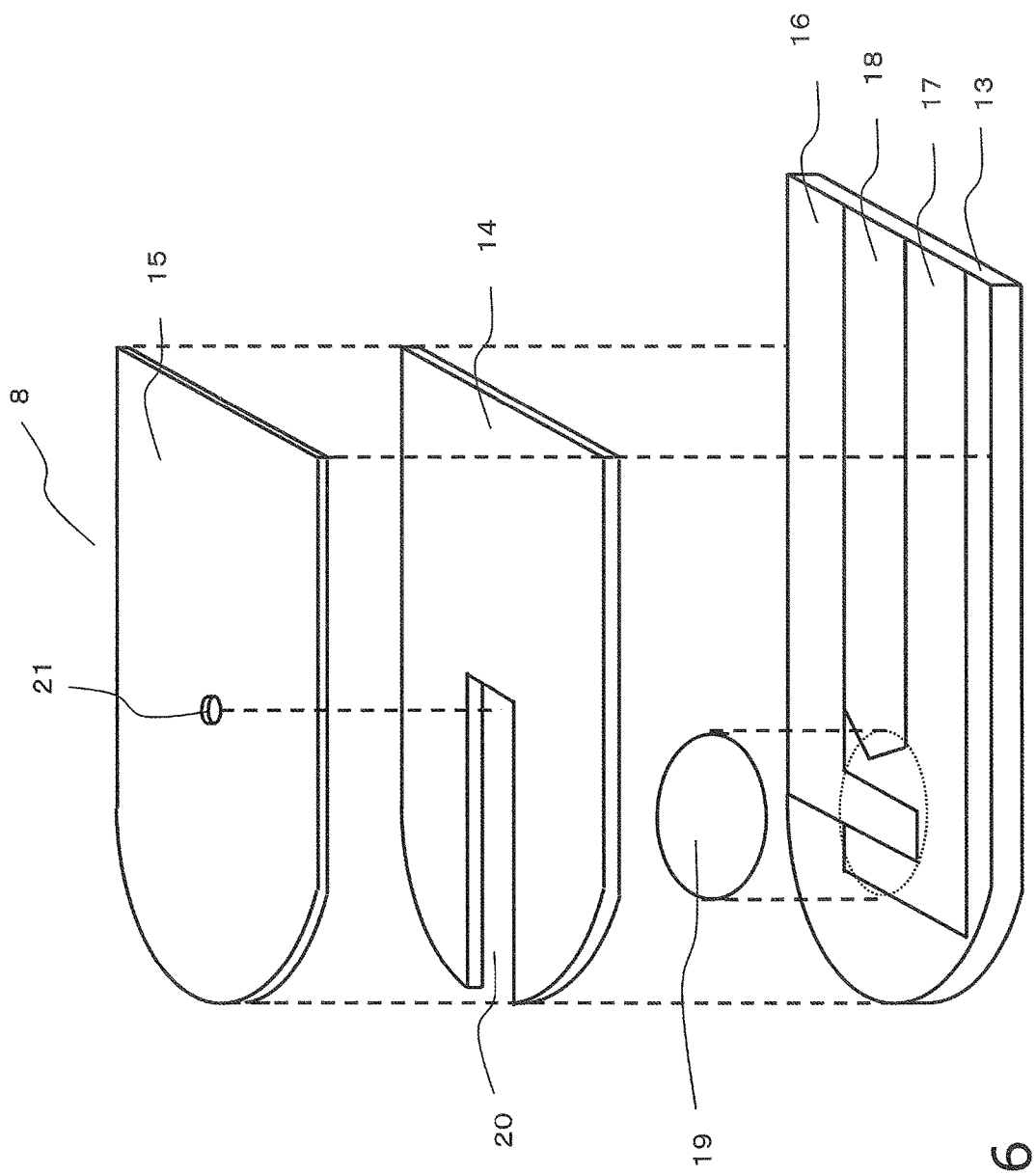
FIG. 6 is an exploded oblique view of the configuration of the sensors stored in the sensor storage container in FIG. 1.
Figure 7:
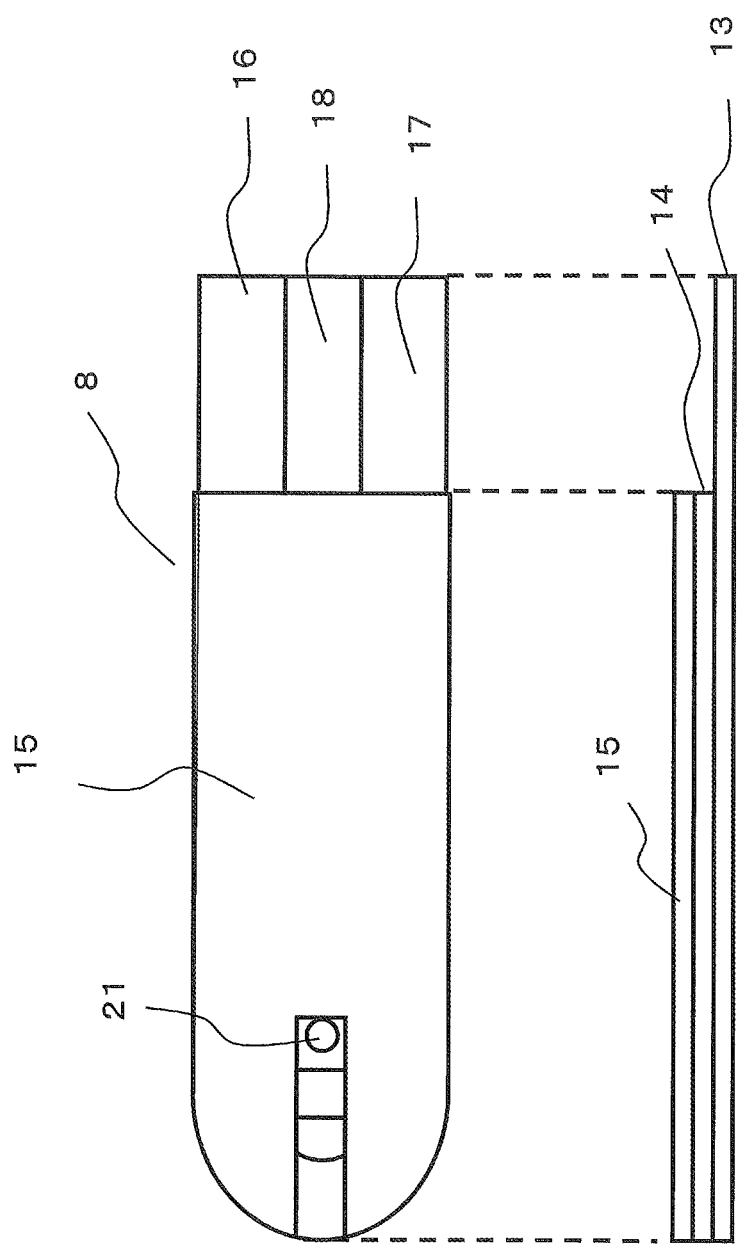
FIG. 7A is a plan view of the configuration of the sensor in FIG. 6.
FIG. 7B is a side view of the configuration of the sensor in FIG. 6.

As shown in FIG. 5, this allows the user to easily grasp the portion of one sensor 8 of the upper end side, and remove that sensor 8.

In this embodiment, the sensors 8 stored in the sensor storage container are each formed by superposing a flat spacer 14 and a flat cover 15 over a base 13.

More specifically, an electrode 16 that serves as a working electrode, an electrode 17 that serves as a counter electrode, and an electrode 18 that serves as a detecting electrode are spaced apart and disposed on the base 13. A reagent 19 is placed over the electrodes 16 to 18 on the first end side of the sensor 8.

Also, a reagent supply path 20 that extends from one end of the sensor 8 to above the reagent 19 is formed in the spacer 14.

Furthermore, an air hole 21 is formed in the portion of the cover 15 corresponding to the rear side of the reagent supply path 20.

That is, if blood is deposited on the first end side of the reagent supply path 20, it will advance under the capillary action of the reagent supply path 20 to the reagent 19. The blood will then react with the reagent 19, and the blood glucose value will thereby be measured. In order to carry out this measurement, the electrodes 16 to 18 are exposed on the second end side of the sensor 8 in order to electrically connect them to the measurement device.

That is, the spacer 14 and the cover 15 are superposed over the base 13 on the first end side of the base 13. Meanwhile, on the second end side, which is on the opposite side from the first end of the base 13, the spacer 14 and the cover 15 are shorter than the base 13, so the spacer 14 and the cover 15 are not superposed over the base 13.

Consequently, the electrodes 16 to 18 are exposed to the outside, without being covered by the cover 15, etc. Also, since the spacer 14 and the cover 15 are not superposed on the second end side of the sensor 8, this end is thinner than the first end side.

As shown in FIGS. 2 and 4, a plurality of the sensors 8 are stored in the inner case 7 so that the thinner second end side is facing downward inside the inner case 7.

Therefore, when there is a change from a state in which the inner case 7 is housed in the container body 1 and the opening/closing lid 2 is closed as shown in FIG. 2, to a state in which the opening/closing lid 2 has been opened, the inner case 7 has risen, and the upper end (first end side) of the sensors 8 are protruding above the top face opening of the container body 1 as shown in FIG. 4, the thinner lower end side (second end side) of the sensors 8 is such that the lower ends of the adjacent sensors 8 are packed closely together.

By contrast, the upper ends of the sensors 8 are spaced farther apart from the adjacent sensors 8 because the lower ends of the sensors are packed so closely together. That is, since the sensors 8 are in a state similar to when a peacock spreads its feathers, the upper ends of one sensor 8 protruding above the top face opening of the container body 1 as shown in FIG. 4 can be easily plucked out as shown in FIG. 5.

The configuration in which the above-mentioned sloped side face 11 and sloped bottom face 12 are sloped in the desired direction also contributes to this spreading apart of the upper ends of the adjacent sensors 8.

In this embodiment, as discussed above, in order to spread apart the upper ends of the sensors 8, the lower end sides of the sensors 8 inserted into the inner case 7 are made thinner than the upper end sides that are grasped with the fingers when the sensors are taken out, so the electrodes 16 to 18 are exposed, without being covered by the spacer 14 and the cover 15.

However, since the electrodes 16 to 18 are inserted facing downward in the inner case 7, a portion of the electrodes 16 to 18 of the sensors 8 is disposed on the bottom face side of the inner case 7. As shown in FIG. 5, this keeps the fingers from touching the electrodes 16 to 18 when the sensors are pulled out.

As a result, this prevents the surfaces of the electrodes 16 to 18 from being soiled, which would happen if the fingers touched the electrodes 16 to 18, and prevents poor electrical connections.

Embodiment 2

The sensor storage container pertaining to Embodiment 2 of the present invention will now be described through reference to FIG. 8.

Figure 8:
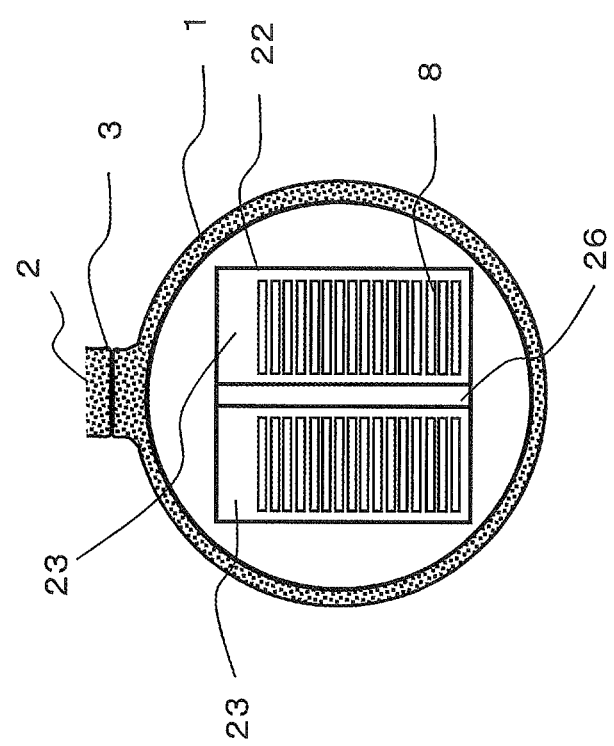
FIG. 8 is a plan view of the configuration of the sensor storage container pertaining to Embodiment 2 of the present invention.

As shown in FIG. 8, in this embodiment an inner case 22 has two (an example of a plurality) storage portions 23 at positions that are symmetrical to the hinge portion 3 in a plan view of the sensor storage container.

The storage portions 23 here are each somewhat wider than the sensors in a direction parallel to the hinge portion 3.

Providing a plurality of these storage portions 23 allows a plurality of sensors 8 to be stored in a neat, vertical state within a single storage portion 23. Thus, as shown in FIG. 5, if the inner case 22 is pulled out above the top face opening of the container body 1, a single sensor 8 can be more easily plucked out.

Embodiment 3

The sensor storage container pertaining to Embodiment 3 of the present invention will now be described through reference to FIG. 9.

Figure 9:
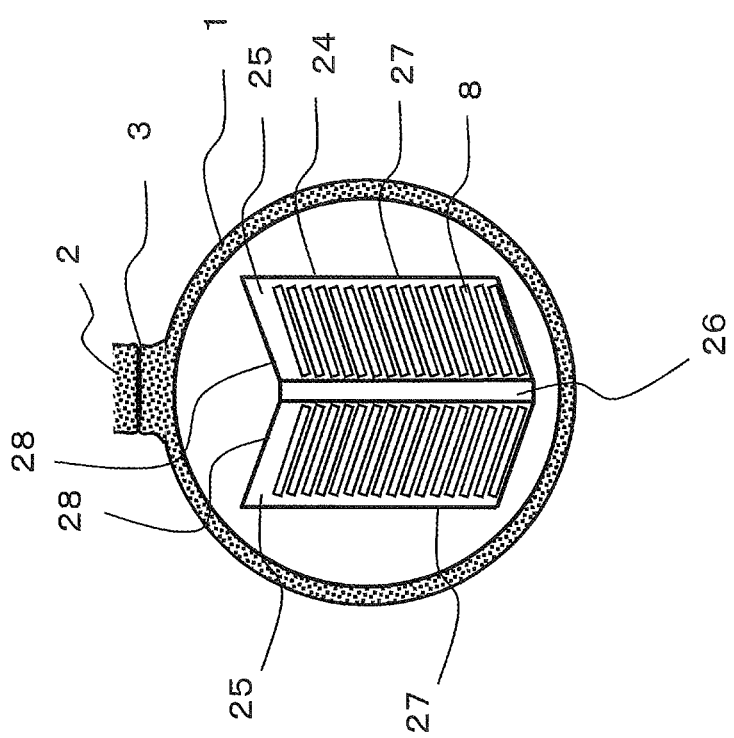
FIG. 9 is a plan view of the configuration of the sensor storage container pertaining to Embodiment 3 of the present invention.

As shown in FIG. 9, in this embodiment an inner case 24 has two (an example of a plurality) storage portions 25 at symmetrical positions with respect to the hinge portion 3.

Furthermore, in this embodiment, two adjacent storage portions 25 within the inner case 24 have one partition wall 26 that separates them, two bilateral portions 27 that are opposite the partition wall 26, and two side face portions 28 that link the bilateral portions 27 together. The side face portions 28 have sloped faces in which the partition wall 26 side is located away from the hinge portion 3, and the bilateral portion 27 side is located closer to the hinge portion 3 side than the partition wall 26 side.

Here, the sensors 8 stored in the left and right storage portions 25 are stored in a state of being inclined in different directions. That is, the sensors 8 stored in the left and right storage portions 25 are stored so that they each face the side face portions 28 that are sloped in plan view as mentioned above.

Consequently, when a single sensor 8 stored in the adjacent storage portions 25 is pulled out, since the orientations of the sensors 8 stored in the adjacent storage portions 25 are different, the sensor can be pulled out more easily.

Embodiment 4

Figure 10:
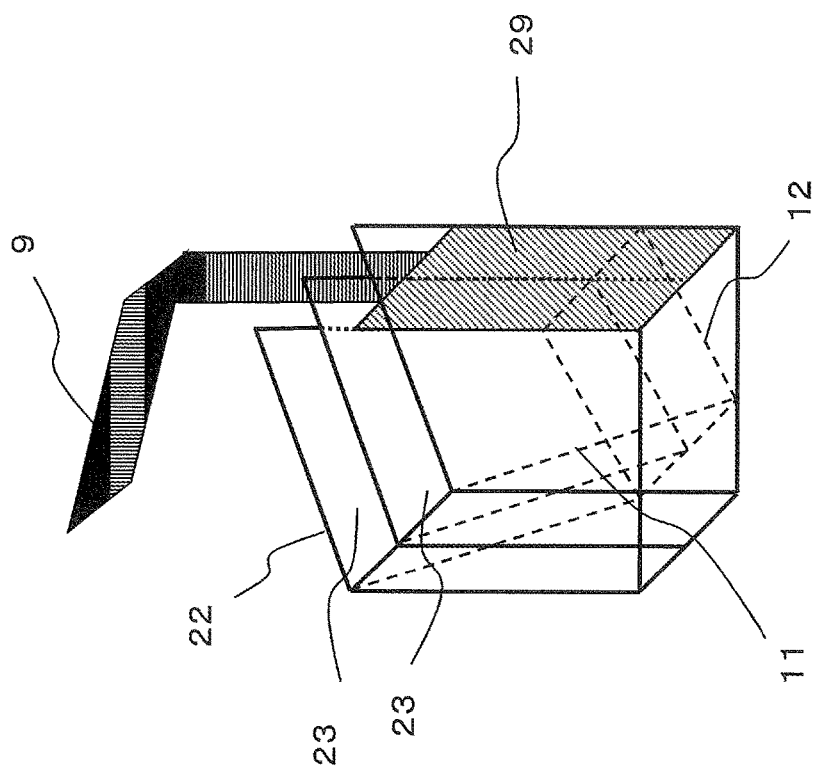
FIG. 10 is a detail view of a part of the inner case of the sensor storage container pertaining to Embodiment 4 of the present invention.

The sensor storage container pertaining to Embodiment 4 of the present invention will now be described through reference to FIG. 10.

In this embodiment, the side of the inner case 22 shown in FIG. 8 that is linked to the flexible linking body 9, that is, the wall 29 of the container body 1, is shorter in height than the other walls that make up the inner case 22. In this state, the first end of the linking body 9 is linked to the upper end of the wall 29.

Consequently, as can be seen from FIG. 4, for example, on the opening/closing lid 2 side, the fingers that pull out the sensor 8 can be inserted farther down because the wall 29 is lower. This allows a single sensor 8 to be pulled out more easily.

Specifically, the fingers that grasp the sensor 8 can be inserted farther down, all the way to the portion where the fingers touch the linking body 9. Thus, because of the configuration shown in FIG. 10, the fingers can be inserted deeper into the inner case 22, allowing a single sensor 8 to be pulled out more easily.

Embodiment 5

The sensor storage container pertaining to Embodiment 5 of the present invention will now be described through reference to FIGS. 11 and 12.

Figure 11:
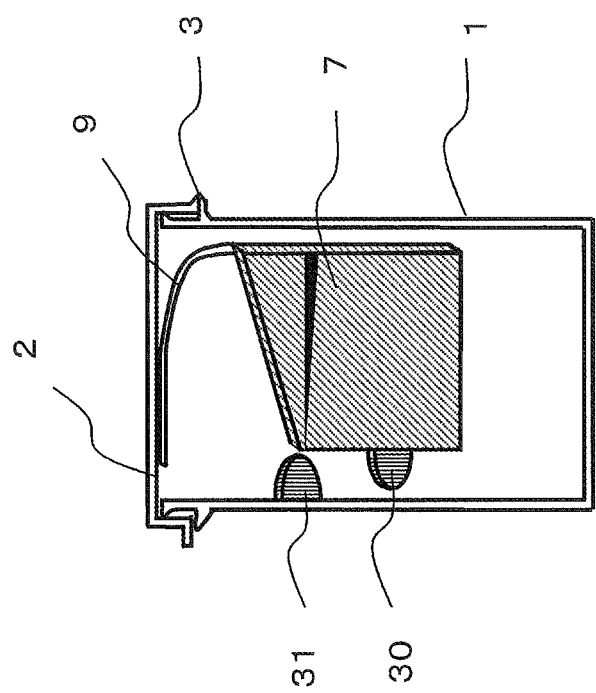
FIG. 11 is a see-through view of the sensor storage container pertaining to Embodiment 5 of the present invention.

In this embodiment, as shown in FIG. 11, the inner case 7 has a protruding stopper 30 on the lower part of the outer peripheral face on the opposite side from the hinge portion 3.

The container body 1 has a stopper 31 on the upper part of the inner peripheral face on the opposite side from the hinge portion 3.

The stopper 30 on the inner case 7 side and the stopper 31 on the container body 1 side are disposed opposite each other, and when the opening/closing lid 2 is closed, as shown in FIG. 11, the stopper 31 is disposed above the stopper 30 across from it.

Figure 12:
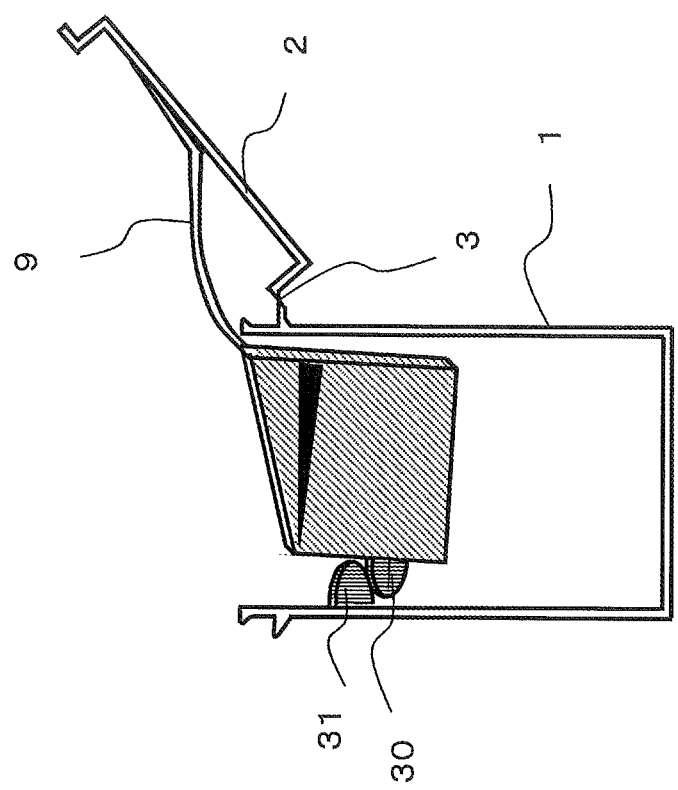
FIG. 12 is a see-through view of the sensor storage container pertaining to Embodiment 5 of the present invention.

As shown in FIG. 12, with the sensor storage container in this embodiment, when the opening/closing lid 2 is opened and the inner case 7 has risen, the top face of the stopper 30 and the bottom face of the stopper 31 come into contact.

Consequently, the stoppers 30 and 31 hits each other when the opening/closing lid 2 is opened, which keeps the inner case 7 from flying out of the container body 1.

INDUSTRIAL APPLICABILITY

As discussed above, the effect of the sensor storage container of the present invention is that a single sensor can be smoothly taken out, and therefore the present invention can be widely applied to containers that store a variety of sensors.

REFERENCE SIGNS LIST 1 container body
2 opening/closing lid
3 hinge portion
4 lip
5 finger
6 finger
7 inner case
8 sensor
9 linking body
10 linking portion
11 sloped side face
12 sloped bottom face
13 base
14 spacer 15 cover
16 electrode
17 electrode
18 electrode
19 reagent
20 reagent supply path
21 air hole
22 inner case
23 storage portion
24 inner case
25 storage portion
26 partition wall
27 bilateral portion
28 side face portion
29 wall
30 stopper
31 stopper

The invention claimed is:

1. A sensor storage container, comprising:
a bottomed cylindrical container body having an opening in its top face;
an opening/closing lid provided to the opening of the container body in an openable and closable state;
a hinge portion that links the container body and the opening/closing lid around a peripheral edge of the opening of the container body, and that opens and closes the opening/closing lid with respect to the container body;
a bottomed inner case that is provided inside the container body and has a vertical peripheral edge on an opening in its top face;
a linking body that links the opening/closing lid with a portion on the hinge portion side of the opening in the inner case; and
a plurality of sensors that are stored vertically along a length direction of the inner case, each of the sensors being formed by superposing a plurality of flat pieces, and in which a lower end of each of the sensors arranged at a bottom face side of the inner case is thinner than an opposing upper end of each of the sensors arranged at an opening side of the inner case in a state of being stored in the inner case; and
wherein the inner case has a partition wall that separates two storage portions, bilateral portions that are opposite the partition wall, and side face portions that connect bilateral portions to each other,
the two storage portions being symmetrical and parallel to the hinge portion in a plan view of the sensor storage container,
one of the bilateral portions being a part of one of the two storage portions,
another one of the bilateral portions being a part of other one of the two storage portions,
the side face portions have a sloped face that is disposed at a position where the partition wall side is away from the hinge portion, and at a position where the bilateral portion side is closer to the hinge portion side than the partition wall side in a plan view, and
the two storage portions are configured to store the sensors in a state of being inclined, wherein the sensors stored in one of the two storage portions are inclined in a different direction than the sensors stored in the other one of the two storage portions, and the sensors face a respective one of the side face portions.

2. The sensor storage container according to claim 1,
wherein the linking body links the inner case and a portion of the opening/closing lid that is away from the end on the hinge portion side.

3. The sensor storage container according to claim 1,
wherein the sensors have a plurality of flat, non-superposed portions, and electrodes that are exposed from the non-superposed portions on an end on the bottom face side of the inner case.

4. The sensor storage container according to claim 1,
wherein the linking body is flexible.

* * * * *